(12) United States Patent
Tominaga et al.

(10) Patent No.: US 7,526,813 B2
(45) Date of Patent: May 5, 2009

(54) GOGGLES

(75) Inventors: Hirofumi Tominaga, Higashiosaka (JP); Noriaki Atake, Higashiosaka (JP); Naoya Aoyama, Higashiosaka (JP)

(73) Assignee: Yamamoto Kogaku Co., Ltd., Osaka (JP)

( * ) Notice: Subject to any disclaimer, the term of this patent is extended or adjusted under 35 U.S.C. 154(b) by 408 days.

(21) Appl. No.: 10/999,311

(22) Filed: Nov. 29, 2004

(65) Prior Publication Data

US 2005/0183191 A1    Aug. 25, 2005

(30) Foreign Application Priority Data

Jan. 29, 2004    (JP)    ............... 2004-020700

(51) Int. Cl.
*A61F 9/00* (2006.01)
(52) U.S. Cl. ................................. 2/13; 2/429
(58) Field of Classification Search ........ 2/12, 2/13, 429; 351/47
See application file for complete search history.

(56) References Cited

U.S. PATENT DOCUMENTS

| | | | | |
|---|---|---|---|---|
| 2,387,821 | A * | 10/1945 | Baratelli et al. | 2/447 |
| 3,419,909 | A * | 1/1969 | Spain | 2/174 |
| 4,934,807 | A * | 6/1990 | Bolle et al. | 351/62 |
| 5,682,621 | A | 11/1997 | Parks et al. | |
| 5,915,542 | A * | 6/1999 | Swiet | 2/441 |
| 6,062,688 | A * | 5/2000 | Vinas | 351/47 |
| 6,094,751 | A | 8/2000 | Parks | |
| 6,641,263 | B2 * | 11/2003 | Olney | 351/62 |
| 6,749,299 | B1 * | 6/2004 | Hsu | 351/62 |
| 6,772,448 | B1 * | 8/2004 | Hockaday et al. | 2/435 |
| 6,793,336 | B2 * | 9/2004 | Min | 351/62 |
| 6,907,617 | B2 * | 6/2005 | Johnson | 2/13 |
| 7,083,276 | B2 * | 8/2006 | Olney | 351/62 |
| 7,091,634 | B2 * | 8/2006 | Yi et al. | 310/62 |
| 7,114,807 | B2 * | 10/2006 | Tagawa | 351/62 |
| 2002/0029408 | A1 | 3/2002 | Lindahl | |

FOREIGN PATENT DOCUMENTS

JP    3092489    3/2003

* cited by examiner

*Primary Examiner*—Katherine Moran
(74) *Attorney, Agent, or Firm*—William L. Androlia; H. Henry Koda

(57) ABSTRACT

Goggles include a goggle body, a frame of the goggle body with a face-side surface, and a cushion member attached to the face-side surface. The cushion member has a shape extending along all or almost all around area on the face-side surface of the frame and is detachable from the frame. The cushion member is readily attachable, removable and replaceable, and further suitable for washing. A come-off prevention member is provided on the frame or the cushion member that gives a reliable attachment between the frame and the cushion member and prevents unwanted coming off or shifting in position of the cushion member. Also, the cushion member has an outer cover that gives reliable airtightness to the goggles.

25 Claims, 11 Drawing Sheets

GOGGLES

TECHNICAL FIELD OF THE INVENTION

This invention relates to goggles which are used for the purpose of protection against dust and the like while skiing or snow boarding, doing motor sports, doing water sports such as canoeing, or in factories.

BACKGROUND ART

In goggles used for the purpose of protection against dust and the like while skiing or snow boarding, doing motor sports, doing water sports such as canoeing, or in factories, a goggle frame have a cushion member on a wearer's face-side surface (hereinafter referred to as a face-side surface) in order to give a comfortable contact to a wearer's face.

This type of conventional goggles in general has a cushion member undetachably glued to a frame of a goggle body. One exception is shown in U.S. Pat. No. 6,094,751, the disclosure of which is herein incorporated by reference. In this prior art specification, a cushion member with a plate-like carrier strip having projecting nibs on its outer face and a spongy strip adhered to an inner face of the carrier strip is detachably attached to a face-side surface of the goggle frame by means of an engagement between the projecting nibs and their counter-holes provided on the face-side surface of the goggle frame.

In the foregoing US patent specification, the cushion member is made up with two sections; one comes in contact with a wearer's brow, and the other comes in contact with the wearer's cheekbones. The two sections cannot be handled as one unit, which therefore causes troublesomeness in attachment, removal and/or replacement.

In addition to it, since the cushion member is made up with the carrier strip and the spongy strip adhered thereto, it is not suitable for washing because washing is liable to damage the carrier strip and/or cause the carrier and spongy strips to separate from each other.

Furthermore, absence of the cushion member at both right and left lateral sides (hereinafter referred to as lateral sides) of the goggle frame (portions corresponding to a wearer's temples) allows air to flow in and out more than necessary and a reliable airtightness cannot be obtained.

Moreover, the engagement between the frame and the cushion member is obtained with the nibs and the counter-holes, or a pair of fabric fasteners provided on the frame and the carrier strip shown in FIG. 5 of the US patent. In either case, the engagement is given only with engaging members provided on the face-side surface of the frame and the outer face of the carrier strip opposing thereto. As a result, the attachment between the frame and the cushion member is not sufficiently reliable, and the cushion member is prone to come off or get out of position when having an impact, for example, because of a wearer's falling down.

SUMMARY OF THE INVENTION

It is hence an object of the present invention to provide goggles in which a cushion member is readily detachable and replaceable, suitable for washing, reliable in airtightness, and a fixed attachment between a frame and the cushion member is ensured so that the cushion member is prevented from coming off the frame and getting out of position when having an impact due to, such as, a wearer's falling down.

Goggles of the present invention have a frame of a goggle body with a face-side surface and a cushion member attached thereto. The cushion member has a shape extending along all or almost all around area on the face-side surface of the frame and is detachable from the frame.

The goggles may have a come-off prevention member either on the frame or on the cushion member. This come-off prevention member is provided on each of the lateral sides of the cushion member and may be formed in a strap through which each of lateral ends of the frame is received. Furthermore, this strap may be hung on a hook provided on each of the both lateral ends of the frame.

The cushion member may be formed with a protection plate and a sponge foam fixed thereto, which are covered with cloth.

A pair of fabric fasteners may be provided along all or almost all around area on the face-side surface of the frame and on a surface of the cushion member which opposes to the face-side surface of the frame.

Alternatively, the face-side surface of the frame and the surface of the cushion member may be respectively provided with plural projections and counter-holes at appropriate intervals.

Moreover, the cushion member may have an outer covering member which covers the outer peripheral edge of the face-side surface of the frame.

BRIEF DESCRIPTION OF THE DRAWINGS

FIG. 9(a) shows a thin cushion member and FIG. 9(b) shows a thick cushion member, and a headband is omitted.

DETAILED DESCRIPTION OF THE INVENTION

Figure 1:
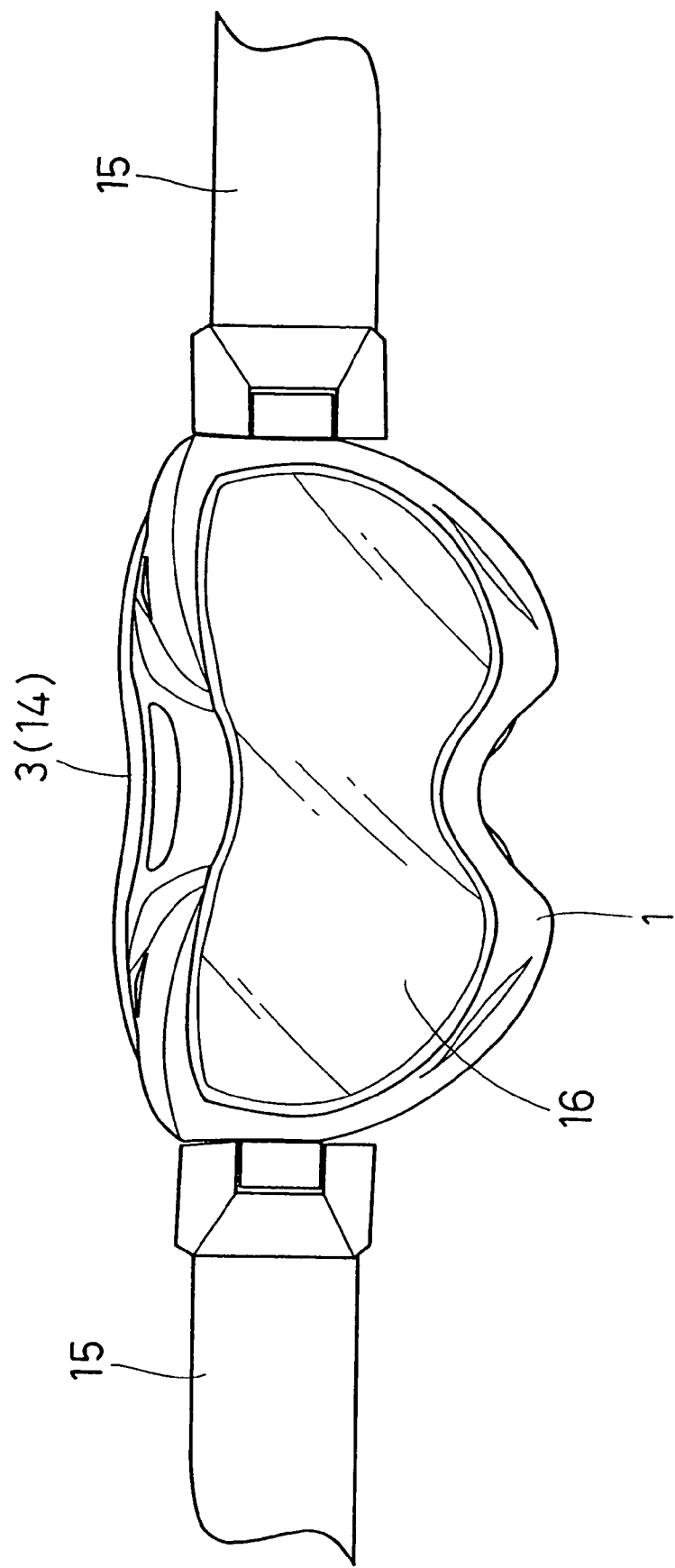
FIG. 1 is a front view of goggles of Embodiment according to the present invention.
Figure 2:
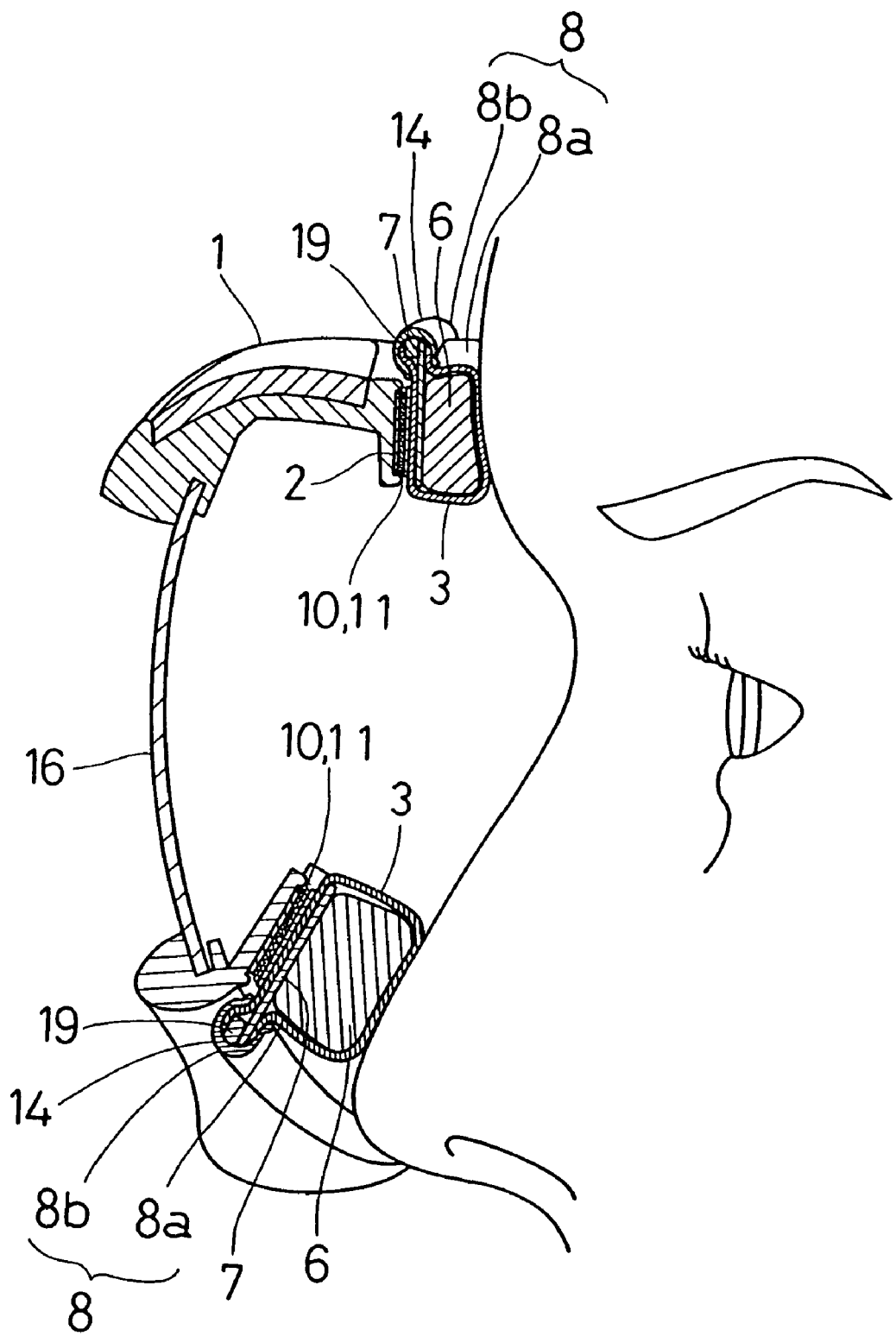
FIG. 2 is a vertical sectional view showing a state that the goggles are put on a wearer's face.

Goggles according to the present invention, as shown in FIGS. 1 and 2, a frame 1 of a goggle body with a face-side surface 2 and a cushion member 3 attached to the face-side surface 2. The cushion member 3 has a shape extending along all or almost all around area on the frame 1 and is detachable from the frame 1.

The illustrated goggles are ski goggles. The goggle body has the frame 1 which covers from around wearer's eyebrows to his or her cheeks and nose and a goggle lens 16 fitted into the frame 1. The both right and left lateral sides of the frame 1 are connected with a headband 15. The illustrated goggles have a single-piece lens, but not limitative thereto, and may have two lens pieces.

Figure 3:
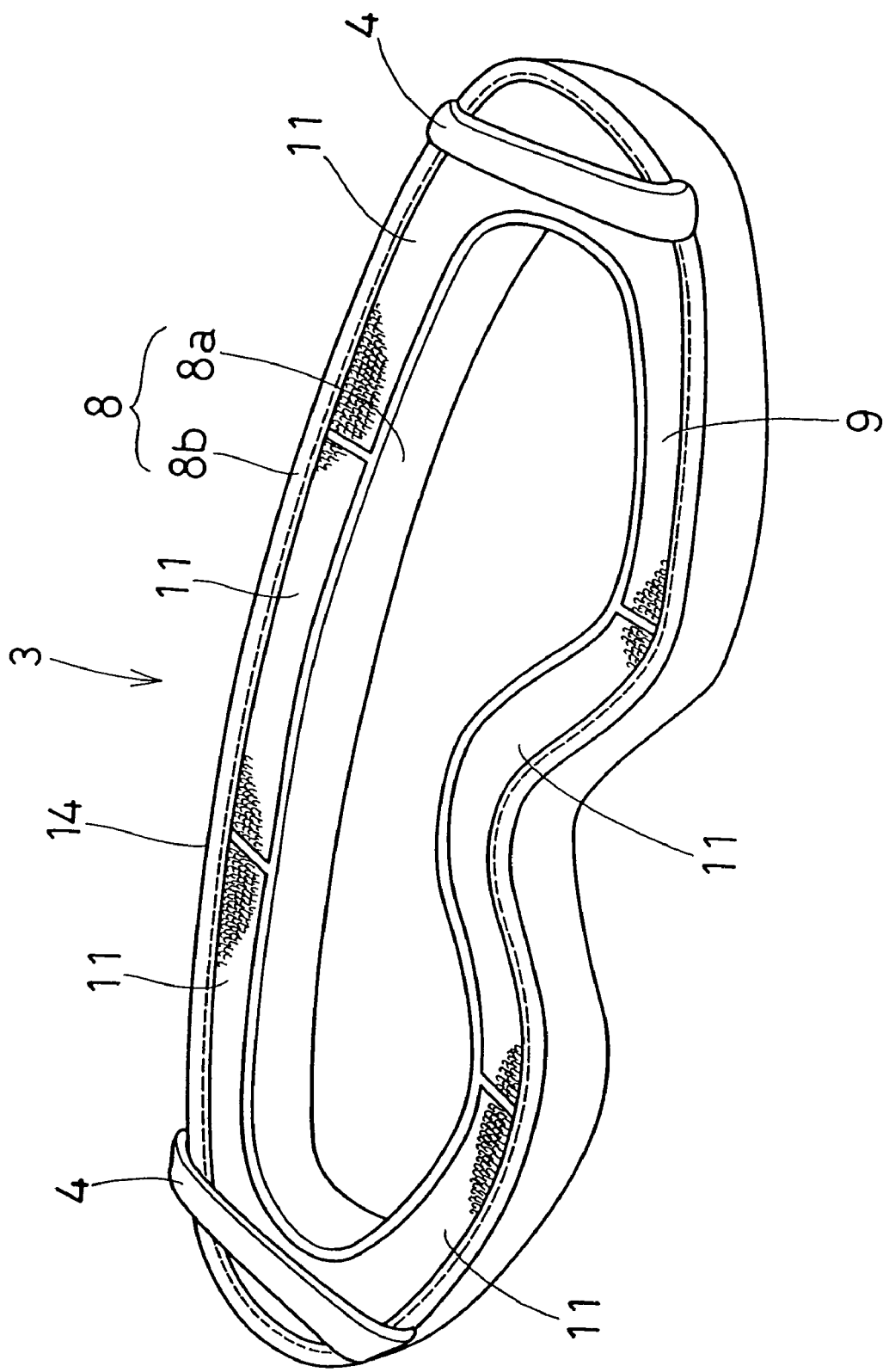
FIG. 3 is a perspective view of a cushion member of the goggles.

The cushion member 3, as shown in FIGS. 2 and 3, has a shape coving and extending along all or almost all around area on the face-side surface 2 of the frame 1, and is made up with a sponge foam 6 and a synthetic resin protection plate 7 attached thereto, which are covered and sewed together with cloth. In this embodiment, the cushion member 3 annularly extends along all or almost all around area on the face-side surface 2, but not limitative thereto, as long as it extends almost all the around area on the face-side surface 2, the shape does not have to be fully continuous, but may have a cut inbetween. In case the shape has a cut portion, it is advisable to make a gap as small as possible.

Figure 4:
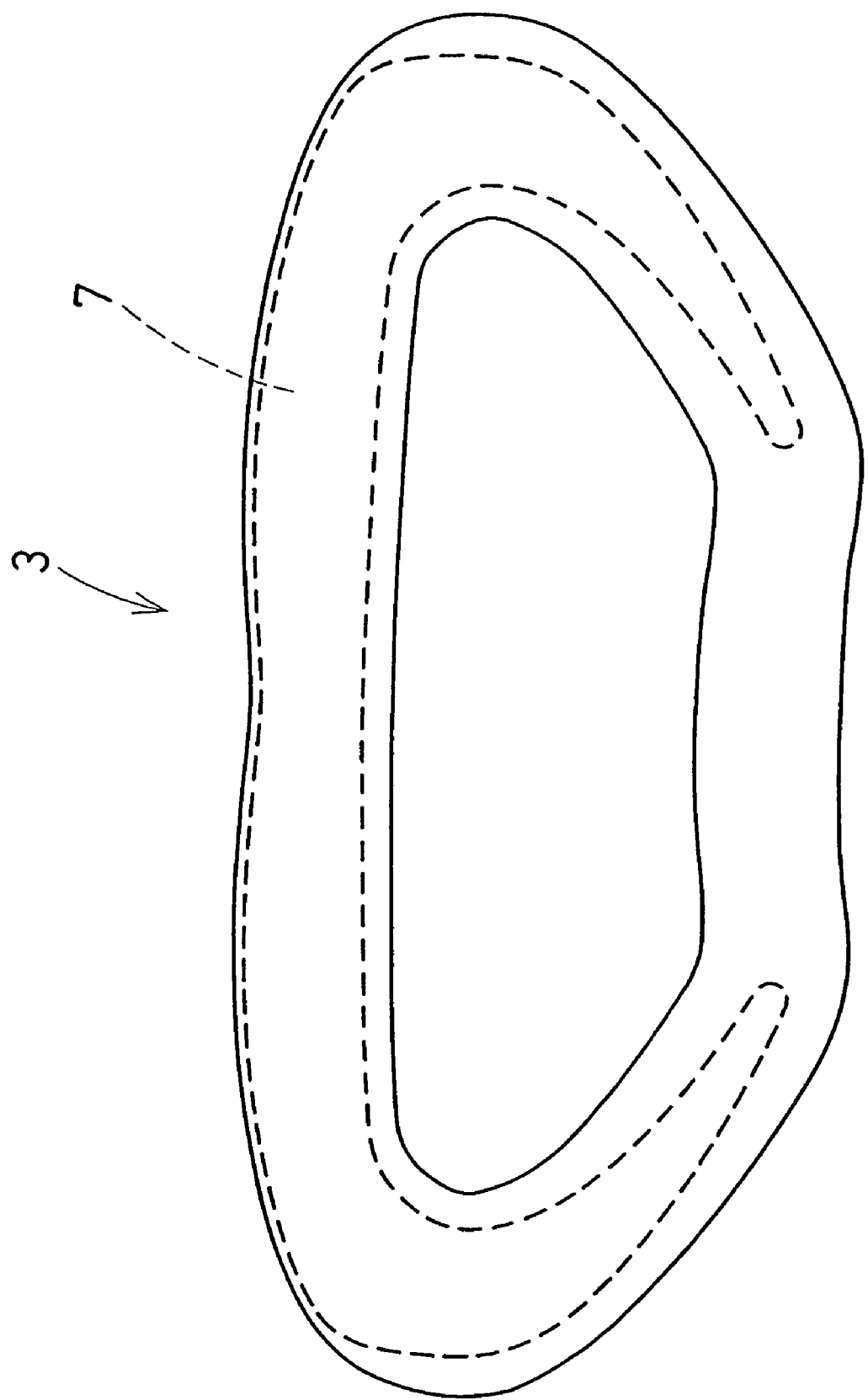
FIG. 4 is a view showing an area of the cushion member to which a protective plate is provided.
Figure 5:
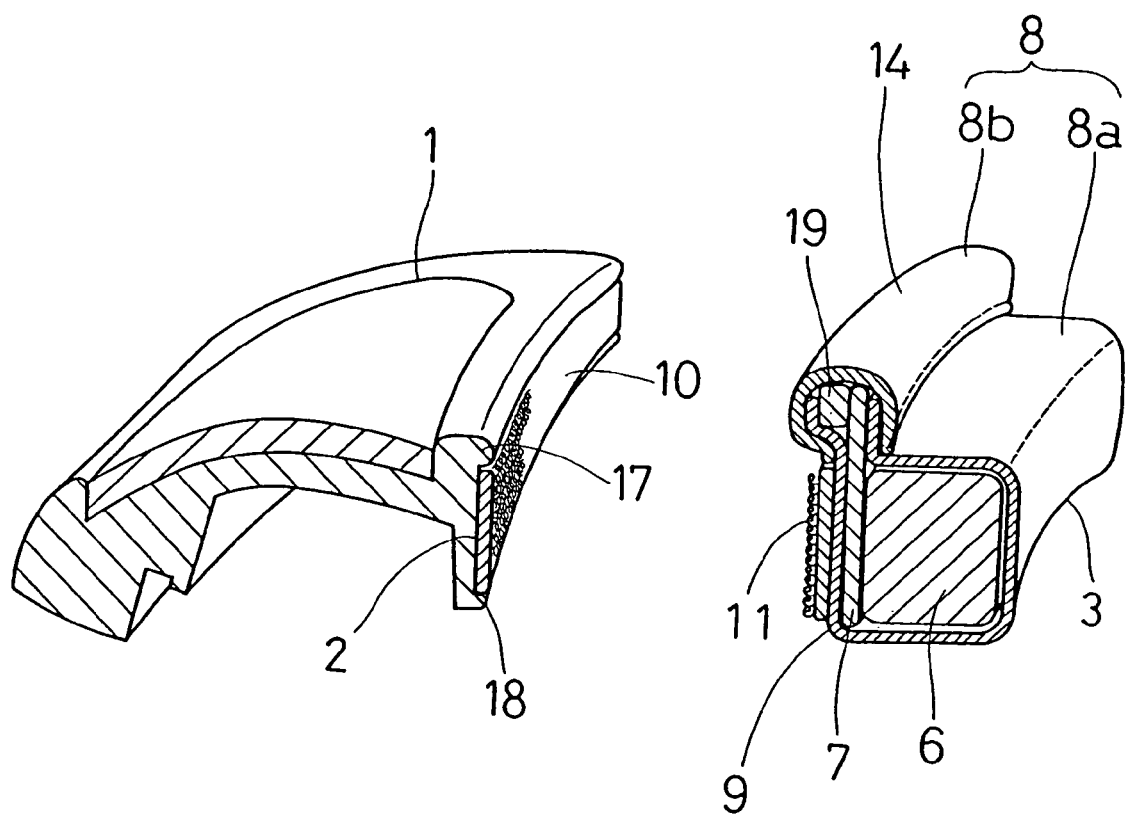
FIG. 5 is a vertical sectional view showing a state in which the cushion member is removed from the frame.
Figure 6:
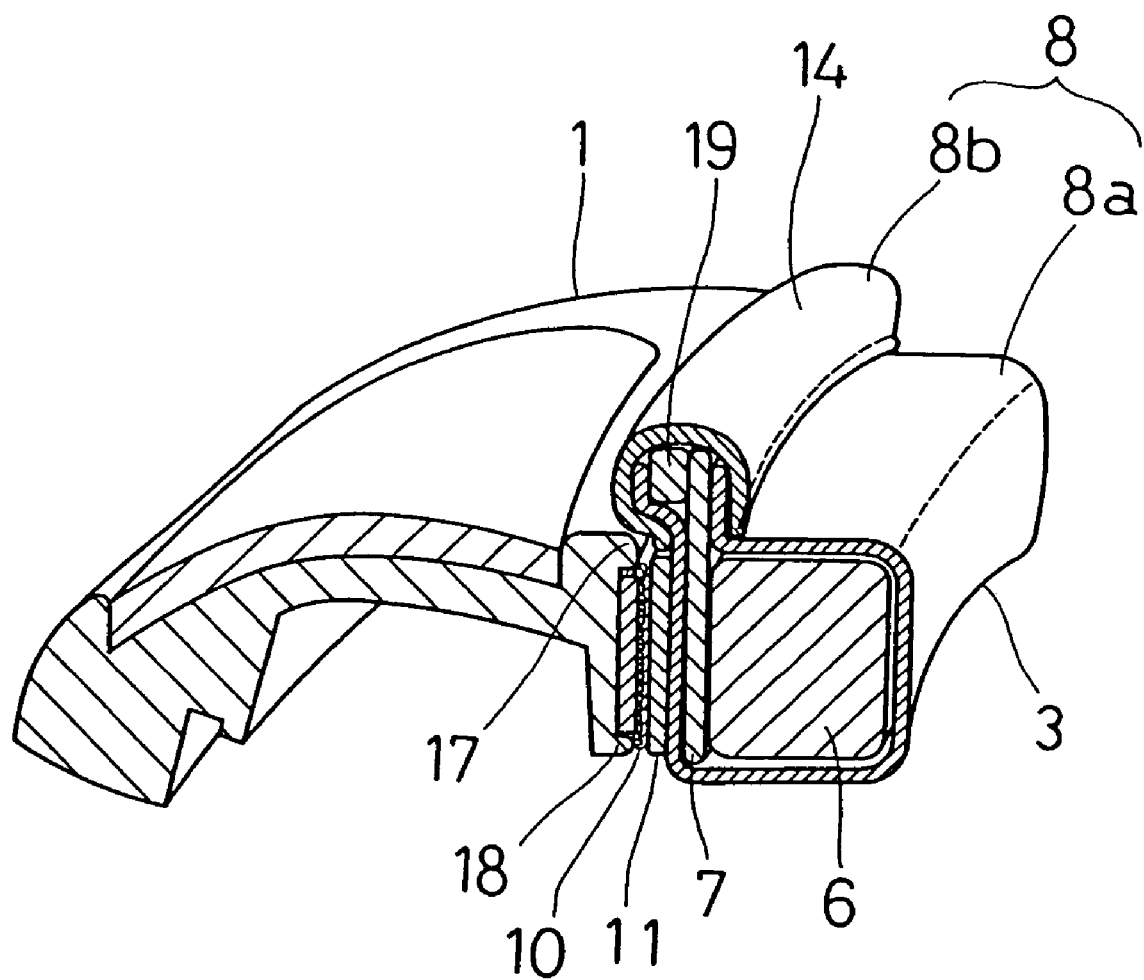
FIG. 6 is a vertical sectional view showing another state in which the cushion member is attached to the frame.

The sponge foam 6 is made of urethane foam and has a section of a substantially square or rectangular shape. The protection plate 7 is made of polyethylene and has a shape to be provided on an area indicated with a dotted line in FIG. 4. The protection plate 7 is adhered to and fixed on one side of the sponge foam 6 opposing to the frame 1. At an upper end of the cushion member 3 (a portion corresponding to a wearer's brow), as shown in FIGS. 5 and 6, an upper part of the protection plate 7 extends higher than and projects from the sponge foam 6.

The cloth member 8 covering the sponge foam 6 has cloth 8a and 8b; the cloth 8a covers around the sponge foam 6 and one side part thereof comes in contact with a wearer's face and the cloth 8b is for hemming. It is preferable that the cloth member 8 is made of water-absorbing, quick-drying synthetic fiber, but not limitative thereto.

The cloth 8a covers the protection plate 7 and the sponge foam 6 in a fashion extending from an upper end of the frame-side surface of the protection plate 7, around the protection plate 7 and the sponge foam 6 and to the other side surface of the protection plate 7, ends of the cloth 8a being spaced from each other, and there is an opened gap between the ends of the clothe 8a near the upper end of the protection plate 7.

The hemming cloth 8b stretches over the foregoing opened gap between the ends of the cloth 8a near the upper end of the protection plate 7 and is sewed and fixed to the cloth 8a.

The cushion member 3 has the foregoing structure in which the sponge foam 6 and the protection plate 7 are covered with the cloth member 8 and this structure prevents deformation and/or damage of the member 3 while attaching, detaching and washing.

All or almost all the around areas on the face-side surface 2 of the frame 1 and a surface 9 of the cushion member 3 opposing to the surface 2 are provided with a paired fabric fasteners 10 and 11. The fabric fastener 10 provided on the frame 1 side is a loop-type nylon fabric fastener and the other fabric fastener 11 provided on the cushion member 3 side is a hook-type polyester fabric fastener or vice versa.

Due to the structural properties of a paired fabric fasteners, there exists space between the connecting sides (i.e. between the loops and hooks). In order to prevent invasion of wind and/or snow through the space and guarantee airtightness, the goggles of the present invention have an outer cover 14 so as to hang over an outer peripheral side of the face-side surface of the frame 1.

More specifically, as shown in FIGS. 5 and 6, the face-side surface 2 of the frame 1 has ribs 17 and 18 of a 1 mm height respectively on an outer and an inner peripheral side. And an outer peripheral side of the cushion member 3 is provided with the outer cover 14. The outer cover 14 is made of the hemming cloth 8b which is sewed to the cloth 8a so as to surround an adhesive double coated tape 19 of a 3 mm thickness provided on a frame-side surface of the protection plate 7 between the spaced upper ends of the cloth 8a. The adhesive double coated tape is made of chloroprene rubber.

The outer cover 14 hangs over an outer side of the outer peripheral side rib 17 on the face-side surface 2 of the frame 1 so as to shield the space between the connecting sides of the paired fabric fasteners 10 and 11, and thereby wind, snow, dust and the like are prevented from invading into an interior space of the goggles.

Figure 10:
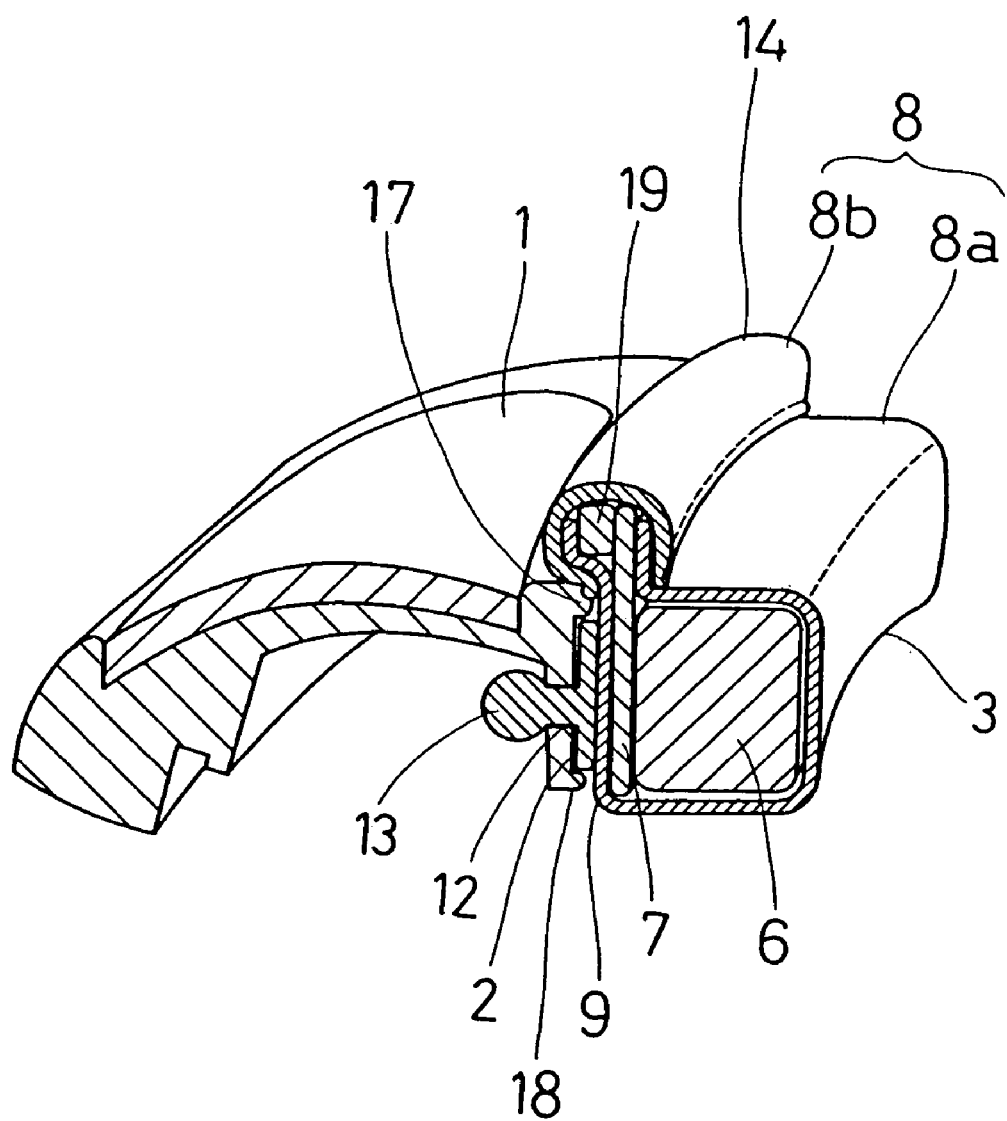
FIG. 10 is a vertical sectional view of another embodiment according to the present invention, in which the cushion member is attached to the frame.
Figure 11:
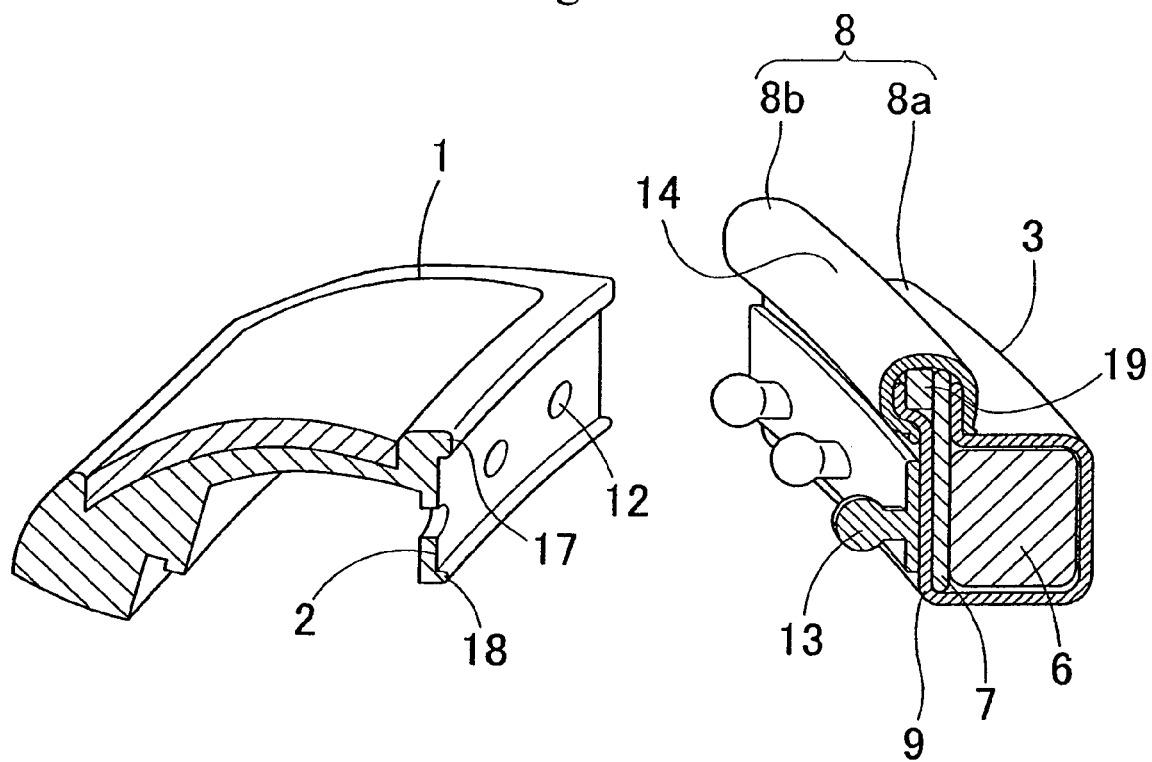
FIG. 11 is a vertical sectional view of the present invention illustrating the attachment of the cushion member to the frame.

FIG. 10 shows another embodiment of engaging the frame 1 and the cushion member 3. Here the face-side surface 2 of the frame 1 and the surface 9 of the cushion member 3 opposing to the face-side surface 2 are respectively provided with holes 12 and projections 13. The projections 13 are pushed into the holes 12 so as to fix the frame 1 and the cushion member 3. In this case, the frame 1 may have plural holes 12 at appropriate intervals and the cushion member 3 has as many projections 13 as the holes 12 at the positions corresponding to the holes 12.

In the cross-sections of FIGS, 10 and 11 is shown the plurality of projections 13 and hole 12, each of the plurality of projections 13 has a spherical portion at its tip, the diameter which is larger than that of the hole 12. The tip spherical portion is forcibly pushed through the hole 12 which deforms while the tip portion is passing, and the projection 13 is fixedly settled in the hole 12 and the frame 1 and the cushion member 3 are fixed together. The hole 12 in this embodiment is a through hole, but not limitative thereto and it may be a non-through hole.

Figure 7:
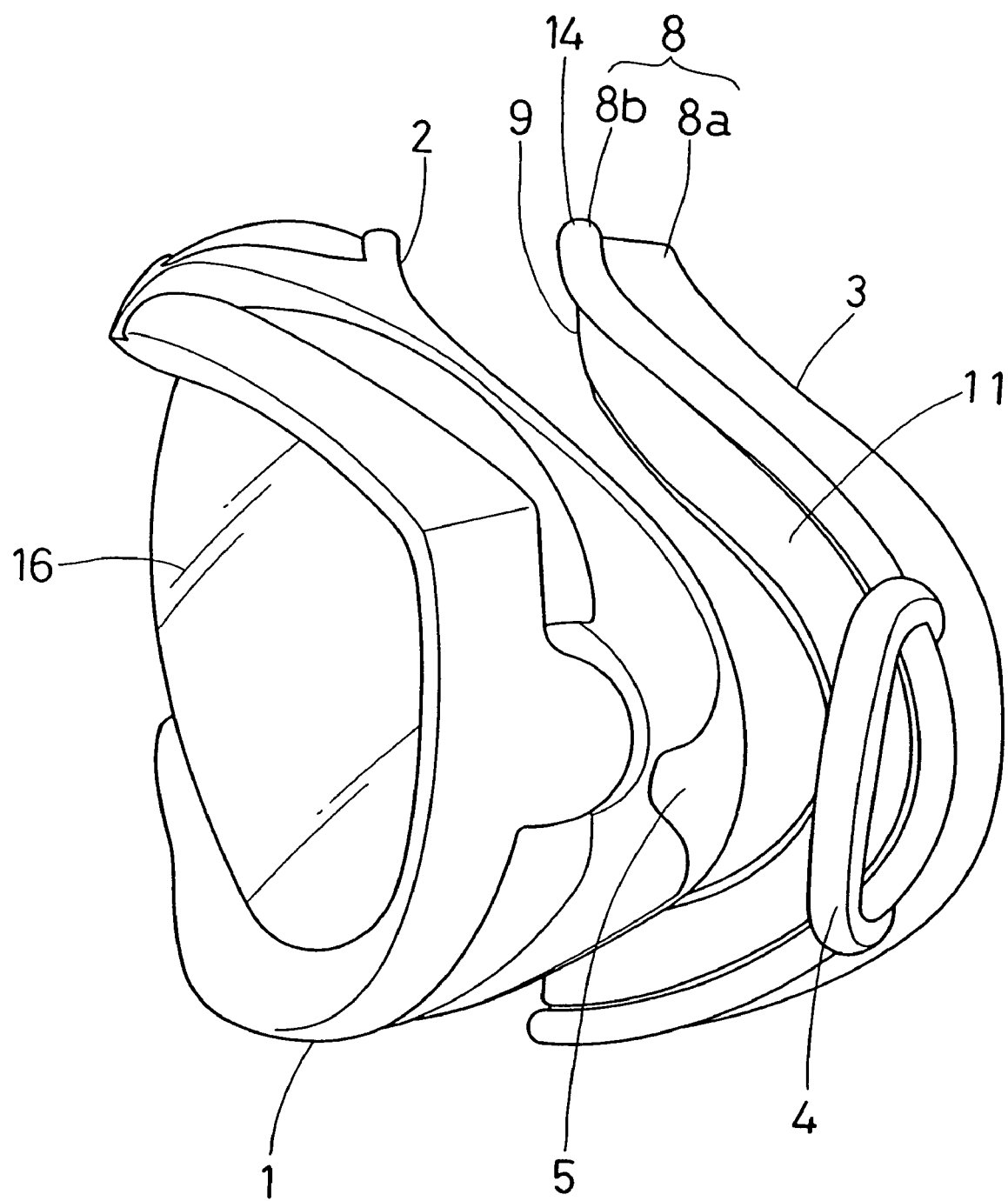
FIG. 7 is a side view of a state in which the cushion member is removed from the frame and a headband is omitted.
Figure 8:
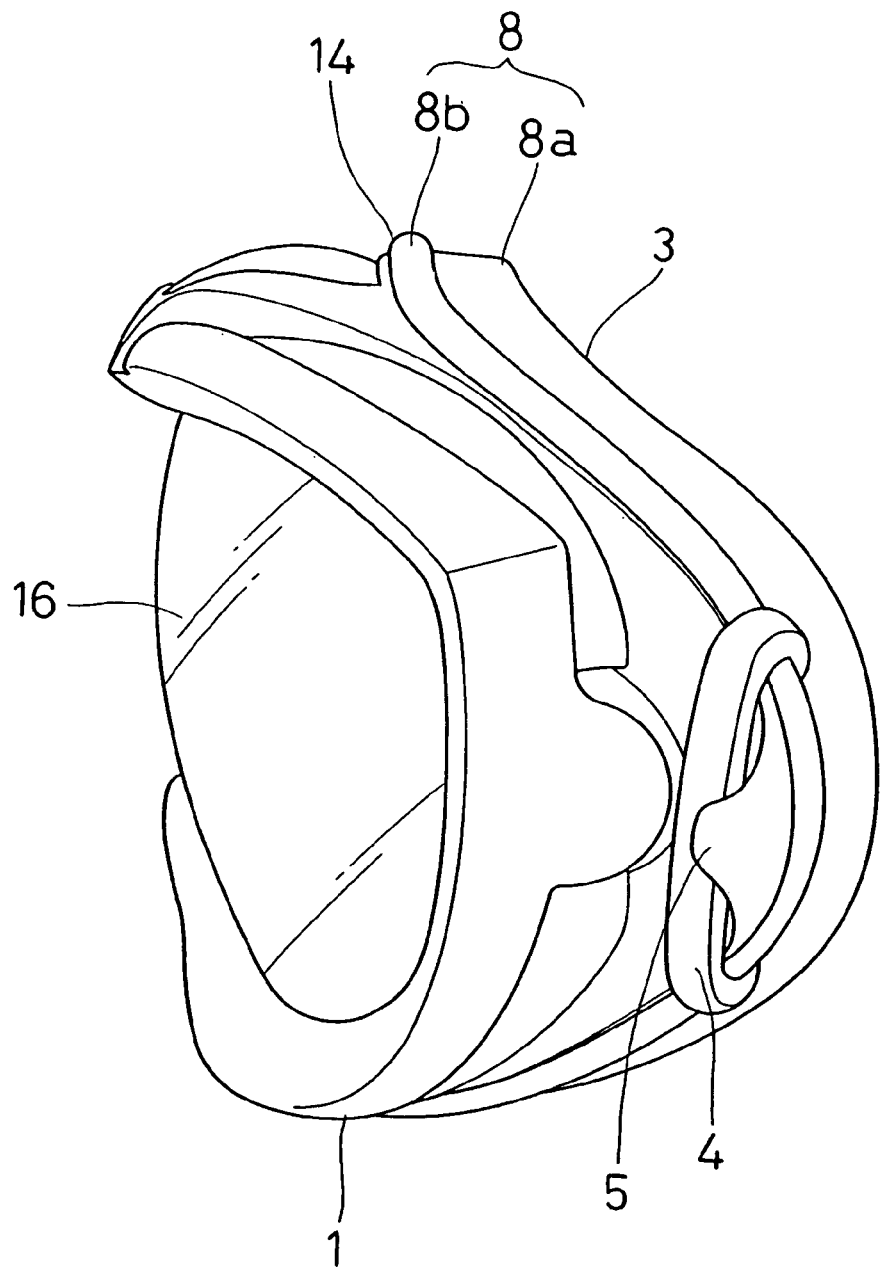
FIG. 8 is a side view of another state where in which the cushion member is attached to the frame and a headband is omitted.

Each of the both lateral sides of the cushion member 3 has a come-off prevention member 4 which prevents the cushion member 3 from coming off the frame 1. As shown in FIGS. 7 and 8, each of both lateral ends of the frame 1 is received through the come-off prevention member 4, and a hook portion 5 forwardly projecting and provided at each of the lateral ends of the frame 1 catches the come-off prevention member 4. The come-off prevention member 4 is made of synthetic leather in a strap-shape and fixedly provided on each of the lateral ends of an outer face of the cushion member 3 (i.e. the surface 9 opposing to the face-side surface 2 of the frame 1), but not limitative thereto. The come-off prevention member 4 of the cushion member 3 may be alternatively provided on the frame 1. For example, such a come-off prevention member 4 may be provided at each of the lateral ends of the frame 1, in a strap-shape, through which each of the lateral ends of the cushion member 3 is received. The come-off prevention member 4 ensures a reliable attachment between the frame 1 and the cushion member 3 and thereby coming-off and shift in position of the cushion member 3 is prevented if an impact due to a wearer's falling down is applied.

The cushion member 3, having the above mentioned structure, is readily attachable and detachable to and from the frame 1. If it is damaged or becomes dirty, the cushion member 3 can be replaceable and washable. The cushion member 3 therefore can be always kept clean. In particular, dirt stuck to a cushion member, for example, waste such as sebaceous matters, dirt of cosmetic foundation and the like, is hard to remove by other than washing. The cushion member 3 of the present invention is washable and thus such dirt can be easily removed.

Furthermore, thickness or resilience of the cushion member 3 may be changeable. For example, a thickness can be selected taking account of a height of a user's nose or a cushion material having higher or lower resilience can be selected depending on a user's preference, so that a user can wear goggles more comfortably.

Figure 9:
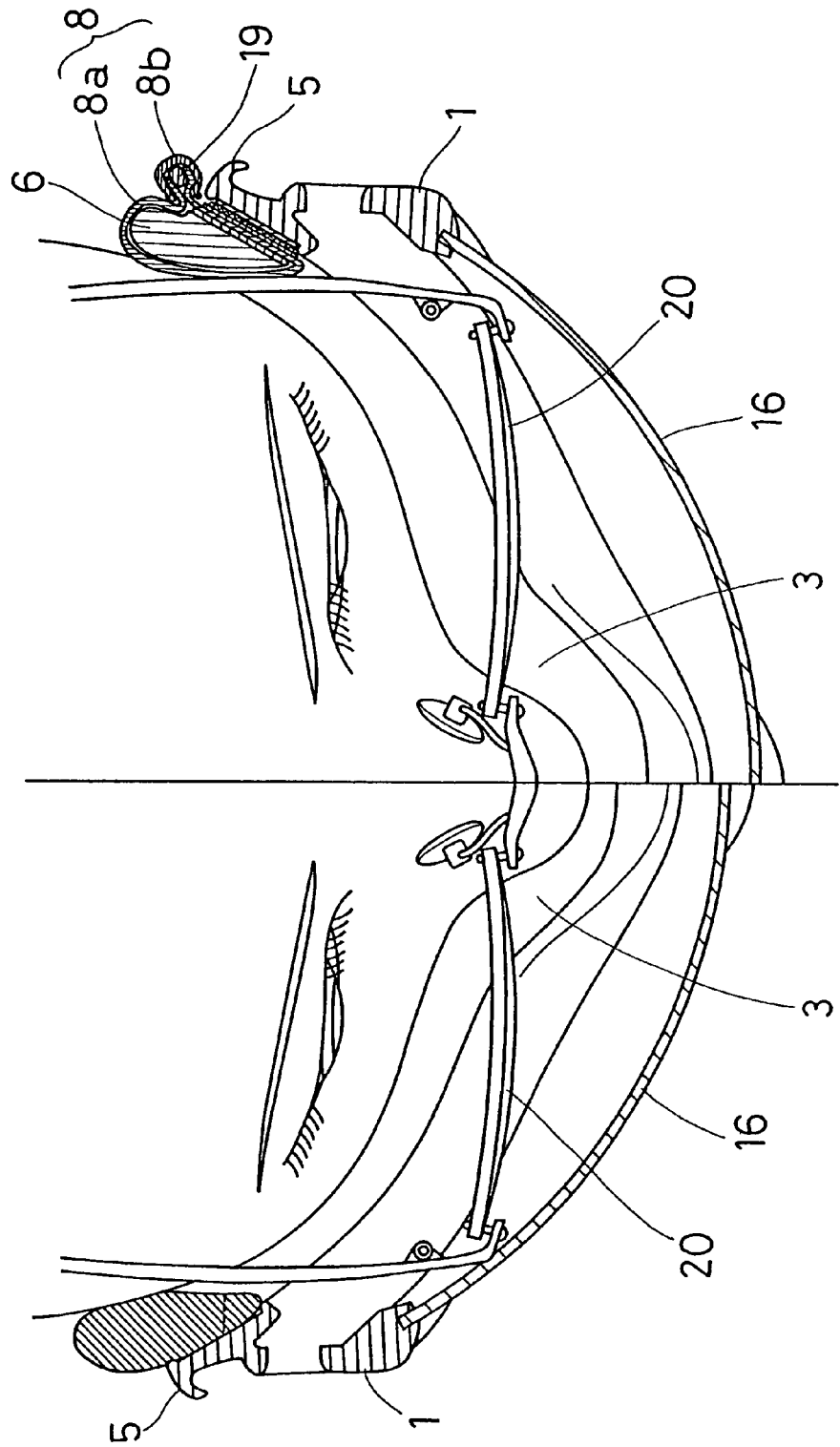
FIGS. 9(a) and 9(b) are transverse sectional views of the states in which the goggles are put on a wearer's face.

The cushion member 3 can have a required thickness. Since an thicker cushion member gives a sufficient distance between the goggle lens 16 and a user's face, he or she can wear the goggles while having a pair of glasses on. In FIG. 9(a), a thinner cushion member 3 provides a smaller distance between the goggle lens 16 and a user's face, the goggle lens 16 and the glasses 20 come in contact with each other. In FIG. 9(b), a thicker cushion member 3 provides a larger distance between the goggle lens 16 and the user's face, and the goggle lens 16 and the glasses 20 do not contact and the user can wear the goggles while having the glasses 20 on.

If material of the cloth member 8 of the cushion member 3 is changed, air-permeability of the cushion member 3 can be adjusted, and a cushion member 3 can be selected depending on weather or climate, or the degree of perspiration. Goggles in which air-permeability is adjustable is specially suitable for motorcyclist's goggles.

The cushion member 3 of the present invention is replaceable when it is damaged or gets dirty, and therefore suitable for rental ski goggles. With replacing an old cushion member with a new one, goggles per se can be used longer. When cloth for dyeing is used as the cloth member 8 of the cushion member 3, the cloth member can be dyed in colors suitable for the frame 1 and goggles can be made with a good appearance.

The goggles of the present application can be applied to snow goggles (for skiing, snow boarding, snow-raking and the like), motor-sports goggles (for motorcycling, driving a buggy and the like), water-sports goggles and industrial goggles used in factories for the purpose of protection against dust and the like.

In the goggles according to the present invention, having the above mentioned structure, the cushion member 3 is made as a single body and has a shape extending along all or almost all the around area on the face-side surface 2 of the frame 1, it is readily attached, removed or replaced. The cushion member 3 can be replaced with another one with an appropriate thickness or color, and further can be readily washed and guarantee a highly reliable airtightness of the goggles.

With the come-off prevention member 4 of the cushion member 3 provided on the frame 1 or the cushion member 3, the cushion member 3 can be prevented from coming off and getting out of position at the time of having an impact due to a user's falling down. The come-off prevention member 4 can be carried out as a strap through which each of the both lateral ends of the frame 1 or the cushion member 3 passes. A hook provided on each of lateral ends of the frame 1 can catch the strap provided on the cushion member 3, which thereby enhances prevention of coming off and shifting in position of the cushion member 3.

The cushion member 3 is made up with the sponge foam 6 and the protection plate 7 attached thereto, which are covered with the cloth member 8, so that deformation and/or damage of the cushion member 3 at the time of attaching, detaching and washing is prevented.

The cushion member 3 is attachable with the frame 1 by mean of a paired fabric fasteners 10 and 11 respectively provided on the entire or almost entire around area of the face-side surface of the frame 1 and the entire of almost entire around area of the surface 9 of the cushion member 3 opposing to the face-side surface 2, or by means of the engagement between plural holes 12 and counter-projections 13 respectively provided at appropriate intervals on the face-side surface 2 of the frame 1 and the surface 9 of the cushion member 3 opposing to the face-side surface 2.

Furthermore, the goggles of the present invention has the outer cover 14 on the cushion member 3 which hangs over the outer peripheral side of the face-side surface 2 of the frame 1, and thus invasion of wind, snow, dust and the like into the interior space of the goggles is prevented.

What is claimed is:

1. Goggles comprising:
   a goggle body,
   a frame of the goggle body with a face-side surface,
   a cushion member for providing a comfortable fit for a wearer attached to the face-side surface, and
   a come-off prevention member of the cushion member provided on either one of the frame and the cushion member, wherein
   the cushion member has a shape extending all or almost all around area on the face-side surface of the frame and is detachable from the frame and the come-off prevention member is a loop strap extending in a substantially vertical direction with respect to transverse direction of the frame and the cushion member, wherein
   the cushion member is made up with a sponge foam and a protection plate attached thereto, and
   a cloth member entirely covers said sponge foam and protection plate whereby the cushion member is washable.

2. The goggles according to claim 1, wherein a paired fabric fasteners are respectively provided on all or almost all around area on the face-side surface of the frame and all or almost all around area on a surface of the cushion member opposing to the face-side surface.

3. The goggles according to claim 2, wherein an outer cover is provided on the cushion member so as to hang over an outer peripheral end of the face-side surface of the frame.

4. The goggles according to claim 1, wherein plural holes and counter-projections are respectively provided at appropriate intervals on the face-side surface of the frame and a surface of the cushion member opposing to the face-side surface.

5. The goggles according to claim 4, wherein an outer cover is provided on the cushion member so as to hang over an outer peripheral end of the face-side surface of the frame.

6. The goggles according to claim 1, wherein an outer cover is provided on the cushion member so as to hang over an outer peripheral end of the face-side surface of the frame.

7. Goggles comprising:
   a goggle body,
   a frame of the goggle body with a face-side surface,
   a cushion member attached to the face-side surface, and
   a come-off prevention member of the cushion member being provided on either side of the frame and the cushion member, wherein
   the cushion member has a shape extending all or almost all around area on the face-side surface of the frame and is detachable from the frame and is made up with a sponge foam and a protection plate attached thereto, and
   said sponge foam and said protection plate are entirely covered with a cloth member, whereby the cushion member is washable.

8. The goggles according to claim 7, wherein a paired fabric fasteners are respectively provided on all or almost all around area on the face-side surface of the frame and all or almost all around area on a surface of the cushion member opposing to the face-side surface.

9. The goggles according to claim 8, wherein an outer cover is provided on the cushion member so as to hang over an outer peripheral end of the face-side surface of the frame.

10. The goggles according to claim 7, wherein plural holes and counter-projections are respectively provided at appropriate intervals on the face-side surface of the frame and a surface of the cushion member opposing to the face-side surface.

11. The goggles according to claim 10, wherein an outer cover is provided on the cushion member so as to hang over an outer peripheral end of the face-side surface of the frame.

12. The goggles according to claim 7, wherein an outer cover is provided on the cushion member so as to hang over an outer peripheral end of the face-side surface of the frame.

13. Goggles comprising:
a goggle body,
a frame of the goggle body with a face-side surface,
a cushion member for providing a comfortable fit for a wearer attached to the face-side surface, and
a come-off prevention member of the cushion member provided on either one of the frame and the cushion member, wherein
the cushion member has a shape extending all or almost all round area on the face-side surface of the frame and is detachable from the frame and the come-off prevention member is a loop strap extending in a substantially vertical direction with respect to transverse direction of the frame and the cushion member, and wherein
the come-off prevention member is provided at each of lateral ends of either one of the frame and the cushion member, through which each of the lateral end portions of either one of the cushion member and the frame is received, wherein
the cushion member is made up with a sponge foam and a protection plate attached thereto, and
a cloth member entirely covers said sponge foam and protection plate whereby the cushion member is washable.

14. The goggles according to claim 13, wherein a paired fabric fasteners are respectively provided on all or almost all around area on the face-side surface of the frame and all or almost all around area on a surface of the cushion member opposing to the face-side surface.

15. The goggles according to claim 14, wherein an outer cover is provided on the cushion member so as to hang over an outer peripheral end of the face-side surface of the frame.

16. The goggles according to claim 13, wherein plural holes and counter-projections arc respectively provided at appropriate intervals on the face-side surface of the frame and a surface of the cushion member opposing to the face-side surface.

17. The goggles according to claim 16, wherein an outer cover is provided on the cushion member so as to hang over an outer peripheral end of the face-side surface of the frame.

18. The goggles according to claim 13, wherein an outer cover is provided on the cushion member so as to hang over an outer peripheral end of the face-side surface of the frame.

19. Goggles comprising:
a goggle body,
a frame of the goggle body with a face-side surface,
a cushion member for providing a comfortable fit for a wearer attached to the face-side surface, and
a come-off prevention member of the cushion member provided on either one of the frame and the cushion member, wherein
the cushion member has a share extending all or almost all around area on the face-side surface of the frame and is detachable from the frame and the come-off prevention member is a loop strap extending in a substantially vertical direction with respect to transverse direction of the frame and the cushion member, and
the come-off prevention member is provided at each of lateral ends of either one of the frame and the cushion member, through which each of the lateral end portions of either one of the cushion member and the frame is received and wherein
the cushion member has the come-off prevention member, the frame has a hook on each of the lateral ends and the hook catches the come-off prevention member, wherein
the cushion member is made up with a sponge foam and a protection plate attached thereto, and
a cloth member entirely covers said sponge foam and said protection plate whereby the cushion member is washable.

20. The goggles according to claim 19, wherein a paired fabric fasteners are respectively provided on all or almost all around area on the face-side surface of the frame and all or almost all round area on a surface of the cushion member opposing to the face-side surface.

21. The goggles according to claim 20, wherein an outer cover is provided on the cushion member so as to hang over an outer peripheral end of the face-side surface of the frame.

22. The goggles according to claim 19, wherein plural holes and counter-projections are respectively provided at appropriate intervals on the face-side surface of the frame and a surface of the cushion member opposing to the face-side surface.

23. The goggles according to claim 22, wherein an outer cover is provided on the cushion member so as to hang over an outer peripheral end of the face-side surface of the frame 24. The goggles according to claim 19, wherein an outer cover is provided on the cushion member so as to hang over an outer peripheral end of the face-side surface of the frame.

25. Goggles comprising:
a goggle body,
a frame of the goggle body with a face-side surface,
a cushion member for providing a comfortable fit for a wearer attached to the face-side surface, and
a come-off prevention member of the cushion member provided on either one of the frame and the cushion member, wherein
the cushion member has a shape extending all or almost all around area on the face-side surface of the frame and is detachable from the frame and the come-off prevention member is a loop strap extending in a substantially vertical direction with respect to transverse direction of the frame and the cushion member, and
the come-off prevention member is provided at each of lateral ends of either one of the frame and the cushion member, through which each of the lateral end portions of either one of the cushion member and the frame is received and wherein
the cushion member has the come-off prevention member, the frame has a hook on each of the lateral ends and the hook catches the come-off prevention member, and
the hook has a shape projecting forwardly.

* * * * *